United States Patent [19]

Buican et al.

[11] Patent Number: 4,905,169
[45] Date of Patent: Feb. 27, 1990

[54] METHOD AND APPARATUS FOR SIMULTANEOUSLY MEASURING A PLURALITY OF SPECTRAL WAVELENGTHS PRESENT IN ELECTROMAGNETIC RADIATION

[75] Inventors: Tudor N. Buican; John C. Martin, both of Los Alamos, N. Mex.

[73] Assignee: The United States of America as represented by the United States Department of Energy, Washington, D.C.

[21] Appl. No.: 366,348

[22] Filed: Jun. 15, 1989

Related U.S. Application Data

[63] Continuation of Ser. No. 201,272, Jun. 2, 1988, abandoned, which is a continuation of Ser. No. 869,179, May 30, 1986, abandoned.

[51] Int. Cl.[4] .......................... G01J 4/00; G01B 9/02
[52] U.S. Cl. ................................. 364/525; 356/327; 356/346; 356/365
[58] Field of Search ............... 364/525, 526, 562, 486, 364/487; 356/327, 346, 349, 351, 355, 357, 365, 366, 369

[56]  References Cited

U.S. PATENT DOCUMENTS

| | | | |
|---|---|---|---|
| 4,086,652 | 4/1978 | Martz | 364/525 |
| 4,138,827 | 2/1979 | Martz | 364/525 |
| 4,162,851 | 7/1979 | Wada | 356/327 |
| 4,173,442 | 11/1979 | Snyder | 356/346 |
| 4,548,500 | 10/1985 | Wyatt et al. | 364/525 |

OTHER PUBLICATIONS

Bouchareine et al., "Interferential Wavelengths Comparison . . . ," SPIE vol. 210 2nd European Congress on Optics Applied to Metrology, 1979, pp. 48–53.
D. H. Martin et al., "Polarised Interferometric Spectrometry for the Millimetre and Submillimetre Spectrum," Infrared Phys. 10, 105–109, Dec. 1969.
Lawrence A. Mafie et al., "Differential Absorption at High Modulation Frequencies Using a Fourier Transform Infrared Spectrometer," Multiplex and/or High Throughput Spectroscopy, SPIE 191, 56–63 (1979).

Primary Examiner—Parshotam S. Lall
Assistant Examiner—Brian M. Mattson
Attorney, Agent, or Firm—Samuel M. Freund; Paul D. Gaetjens; William P. Moser

[57]  ABSTRACT

An apparatus and method simultaneously measures a plurality of spectral wavelengths present in electromagnetic radiation. A modulatable birefringent optical element is employed to divide a polarized light beam into two components, thereby producing a phase difference in two resulting light beams such that the two beams can be made to interfere with one another when recombined, the interference pattern providing the wavelength information required for the analysis of the incident light. The interferometer thus created performs in a similar manner to a Michelson interferometer, but with no moving parts, and with a resolution dependent on the degree of phase shift introduced by the modulator.

36 Claims, 8 Drawing Sheets

METHOD AND APPARATUS FOR SIMULTANEOUSLY MEASURING A PLURALITY OF SPECTRAL WAVELENGTHS PRESENT IN ELECTROMAGNETIC RADIATION

This is a continuation of application Ser. No. 201,272 filed June 2, 1988, which is a continuation of application Ser. No. 869,179 filed May 30, 1986.

BACKGROUND OF THE INVENTION

The invention described herein relates generally to structures and methods for measuring electromagnetic radiation and, more particularly, to structures and methods for simultaneously measuring a plurality of spectral wavelengths present in fluorescence produced when at least one light source excites individual particles moving sequentially through the fluorescence excitation region of a flow cytometer. This invention is the result of a contract with the Department of Energy (Contract No. W-7405-ENG-36).

The subject invention is an apparatus for receiving and analyzing electromagnetic radiation having a plurality of wavelengths in a timescale on the order of 0.01 to 0.1 ms. In its simplest embodiment, the apparatus includes a polarization interferometer which derives its resolution from a birefringent element capable of being modulated at greater than 50 kHz, in contrast to the usual slow mechanical scan of an interferometer mirror. It is well known that the spectral resolution of an interferometer based spectrometer is related to the maximum path difference in its interferogram. In the subject invention, a varying path difference is provided by the different indices of refraction for radiation polarized along the principal axes of the modulatable birefringent element. That is, if radiation undergoing investigation is either polarized to begin with or is passed through a polarizing element not having its polarization axis parallel to or orthogonal to either of the two principal axes of the birefringent element, this radiation will be resolved into two substantially collinear beams, each having its polarization axis directed along one of the principal axes. Since the index of refraction for radiation polarized along each of these axes is different, the difference being a time-varying function of time determined by the frequency at which the birefringent element is modulated, a time-varying phase shift is introduced between the components traveling through the birefringent element. Introducing this phase shift is equivalent to introducing a path difference in a conventional interferometer. However, since the birefringent element can be rapidly modulated, a rapidly varying phase shift is introduced, thereby effectively performing the introduction of a path difference in a very short timescale. This becomes important when one wishes to investigate transient phenomena which are not repetitive, such as the rapid analysis of emission from single particles in order to make separation decisions based on certain characteristics in a flow cytometer system. The two phase-shifted beams are then mixed after passing through a second polarizer which selects a single polarization for the two substantially collinear, phase-shifted components. An interference pattern characteristic of the spectral distribution of the radiation under investigation is produced.

Polarization modulators are known in the art. However, the phase shifts introduced by such modulators are ¼-wavelength of the light employed and not the several wavelengths required and taught by the subject invention in order to obtain reasonable resolution.

U.S. Pat. Nos. 4,086,652 and 4,138,727 to Martz disclose a system for analyzing time-varying phenomena of a repetitive nature. The complete interferogram is obtained by dividing the time period of interest into small time intervals and revisiting a particular interval repeatedly until the desired spectroscopic resolution and signal-to-noise ratio are produced by mechanically scanning a mirror of the interferometer. The reason that any useful spectroscopic information is generated results from the repetitive nature of the phenomenon under investigation, since the scan may effectively be continued for as long as desired, thereby permitting arbitrarily good resolution to be obtained, within the characteristics of the optical system.

"Polarised Interferometric Spectrometry for the Millimetre and Submillimetre Spectrum," by D. H. Martin and E. Puplett, Infrared Physics 10, 105 (1969) discloses the use of polarizers for splitting a light beam into two components and for introducing a path difference therein before recombination thereof for the purpose of interferometric spectrometry. No birefringent modulator apparatus is suggested for rapidly performing the equivalent function of providing a variable or scannable path difference between the components. This result is presumably achieved by mechanically moving the polarizers. "Differential Absorption at High Modulation Frequencies Using a Fourier Transform Infrared Spectrometer," by L. A. Nafie and D. W. Vidrine, Multiplex and/or High Throughput Spectroscopy, SPIE 191, 56 (1979), discloses a birefringent element used to modulate linearly polarized light. However, the purpose of so doing is to analyze the linear and circular dichroism of the sample and not to provide a substitute for mechanically sweeping the mirror to obtain a Fourier spectrum.

The present invention is of particular value when used with flow cytometers. Measurements of the fluorescence from fluorochromes (fluorescent dyes) provide quantitative information about the cell components to which the dyes are bound. Flow cytometers can measure cellular properties such as cell size, DNA content, protein content and cell membrane permeability. They can also measure cellular antigens and the shape, size and DNA content of individual chromosomes. The analysis of cells stained simultaneously with several fluorochromes provides the phenotypic information that can be obtained with the particular fluorochromes and allows cell sorting on the basis of this phenotypic description.

Multiple laser flow cytometers have generally used two or three lasers to excite the same number of fluorochromes. In conventional flow cytometers, each fluorochrome produces fluorescence detected by a separate detector. The number of fluorochromes and the number of detectors are usually the same. The number of detectors represents the number of spectral channels of a conventional flow cytometer.

The increasing availability of new monoclonal antibodies which recognize many different antigens, of fluorochromes which specifically bind to various cell components, and of fluorochromes whose emission and/or excitation spectra change as a result of changes in the physiological state of cells make the development of flow cytometers with an increased number of spectral channels highly desirable. The spectral resolution achievable with conventional flow cytometers is limited by the decrease in detection sensitivity which accompanies any reduction in the spectral range of the fluorescence detectors. This decrease in sensitivity is aggravated in systems with sequential optical filters, since losses increase for each additional detector. No one has published the achievement of an acceptable signal-to-noise ratio for a flow cytometer having more than five spectral channels.

SUMMARY OF THE INVENTION

One object of the present invention is to provide a method and apparatus for simultaneously measuring a plurality of spectral wavelengths present in fluorescence.

Another object of the invention is to simultaneously measure fluorescence over a large number of spectral channels while ensuring adequate sensitivity in each spectral channel.

Still another object of the invention is to increase the spectral resolution of a multiple light source flow cytometer.

Yet another object of the invention is to simultaneously measure a plurality of spectral wavelengths present in electromagnetic radiation.

To achieve the foregoing and other objects, and in accordance with the purposes of the present invention, as embodied and broadly described herein, there is provided an apparatus and method for simultaneously measuring a plurality of spectral wavelengths present in fluorescence.

The apparatus comprises a first polarizer for receiving the fluorescence having an electric field disposed in an arbitrary direction and for defining a first direction for the electric field of the fluorescence transmitted therethrough. A modulatable birefringent element receives the polarized light transmitted through the first polarizer. The birefringent element has first and second principal optical axes along which the electric field of the transmitted polarized light is resolved into first and second components. The light wave corresponding to each of the resolved electric field components travels at a different velocity, so that two first light waves, having different electric field directions and a shift in phase greater than one wavelength of the longest wavelength component of the fluorescence, emerge from the birefringent element. A second polarizer receives the two first light waves emerging from the birefringent element and resolves their electric fields along a second direction, so that two second light waves emerge plane polarized and with the same direction of polarization. A modulator driver modulates the birefringent element such that resolution suitable for measurement of the plurality of spectral wavelengths is achieved. A detector receives the two second light waves emerging from the second polarizer and interacts therewith to produce an electrical signal characteristic of the interference pattern generated as a result of the interference of the two second light waves having different phase and emerging from the birefringent element. A receiving and separating system receives the electrical signal from the detector and separates the signal into its spectral components.

One advantage of the present invention is that a flow cytometer with more than five spectral channels can simultaneously measure fluorescence produced when one or more light sources excite biological particles stained with more than five fluorochromes.

Another advantage of the invention is that the spectral resolution and measurement capability of a flow cytometer are greatly improved.

Still another advantage of the invention is that spectrum of the collected fluorescence is computed very quickly.

Another advantage of the invention is that a single detector can be used to detect fluorescence from many fluorochromes.

Yet another advantage of the invention is that the spectral information for each spectral channel can be computed separately.

Still another advantage of the invention is that spectral analysis can be performed without adjusting optical components or using optical filters.

Another advantage of the invention is that a multiple laser flow cytometer can be used with only one or two detectors.

Still another advantage of the invention is that the spectral response of each spectral channel can be modified.

Another advantage of the invention is the cost, complexity and size of a multiple laser detection system are reduced.

Yet another advantage of the invention is that electronic components for only two detectors are required for use with a multiple laser flow cytometer.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings.

DETAILED DESCRIPTION OF THE INVENTION

Figure 1:
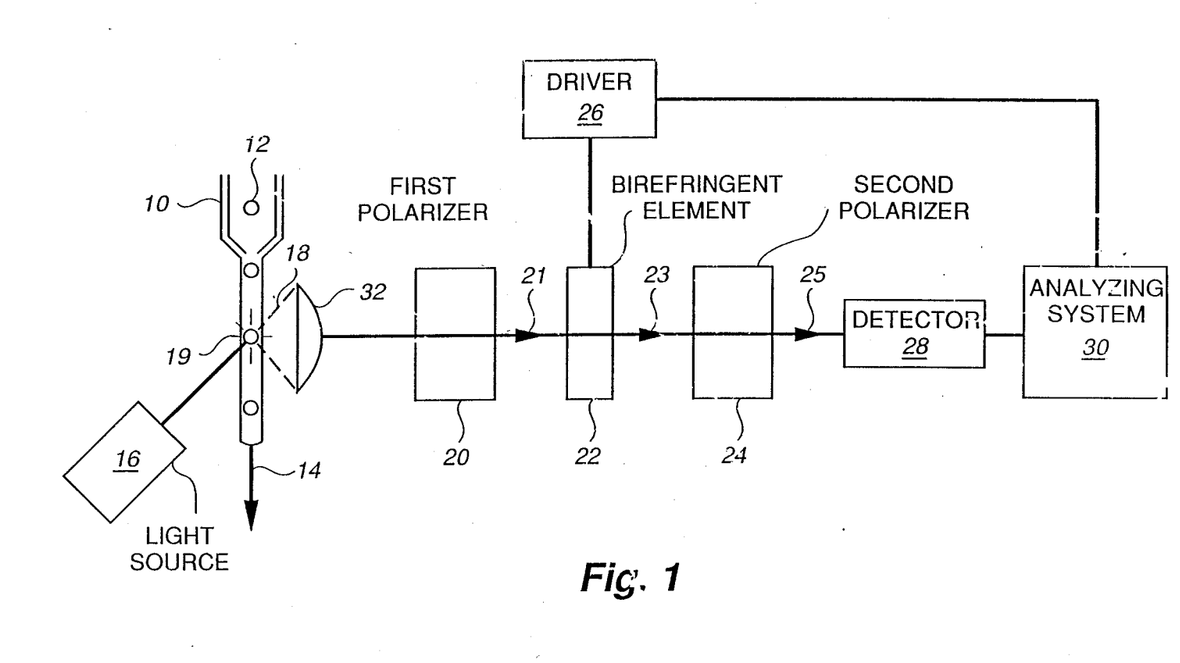
FIG. 1 shows a schematic view of an embodiment of the invention.

Reference is now made to FIG. 1 which shows a schematic view of an embodiment of the invention. The apparatus of the present invention is shown in combination with portions of a flow cytometer 10 through which individual particles 12 move sequentially. The direction of movement of the particles 12 is indicated by arrow 14. Flow cytometer 10 includes at least one light source 16, which may be a laser. The present invention is an apparatus for simultaneously measuring a plurality of spectral wavelengths present in fluorescence, indicated by dashed line 18, produced when a light source 16 excites individual particles 12 moving sequentially through the fluorescence excitation region 19 of flow cytometer 10.

The apparatus in accordance with the present invention includes a first polarizer 20 for receiving the fluorescent light 18 and for defining a first direction for the electric field of the polarized light 21 which passes through first polarizer 20. A modulatable birefringent element 22 receives the polarized light 21 from first polarizer 20. Birefringent element 22 has first and second optical axes, shown in FIG. 2, along which the electric field of the polarized light 21 is resolved into two components. The light wave corresponding to each of the resolved electric field components travels at a different velocity, so two light waves, indicated by arrow 23, having different electric field directions and a shift in phase greater than approximately one wavelength of the longest wavelength component of the fluorescent light 18, emerge from birefringent element 22. A second polarizer 24 receives the two light waves 23 emerging from birefringent element 22 and resolves their electric fields along a second direction, so that two light waves, indicated by arrow 25, emerge therefrom plane polarized and with the same direction of polarization. First polarizer 20, birefringent element 22 and second polarizer 24 make up the interferometer of the present invention. A modulator driver 26 modulates birefringent element 22 such that resolution suitable for measurement of the plurality of spectral wavelengths is obtained during the time in which an individual particle 12 travels through the excitation region 19 of flow cytometer 10.

A first detector 28 receives the light waves 25 emerging from second polarizer 24 and interacts therewith to produce an electrical signal characteristic of the interference pattern generated as a result of the recombination of the two light waves 23 having different phase and emerging from the birefringent element 22. A receiving and analyzing system 30 receives the electrical signal from first detector 28 and quantitatively analyzes the signal into its spectral components.

Particles 12 can be biological particles such as chromosomes. Particles 12 can be unstained, in which case the fluorescence 18 which is detected is intrinsic fluorescence, sometimes called autofluorescence. Particles 12 can be stained with one or more fluorochromes. A first lens 32 can be used to collect the fluorescence 18 and directs it towards first polarizer 20. First lens 32 is located between first polarizer 20 and the flow cytometer 10.

Figure 2:
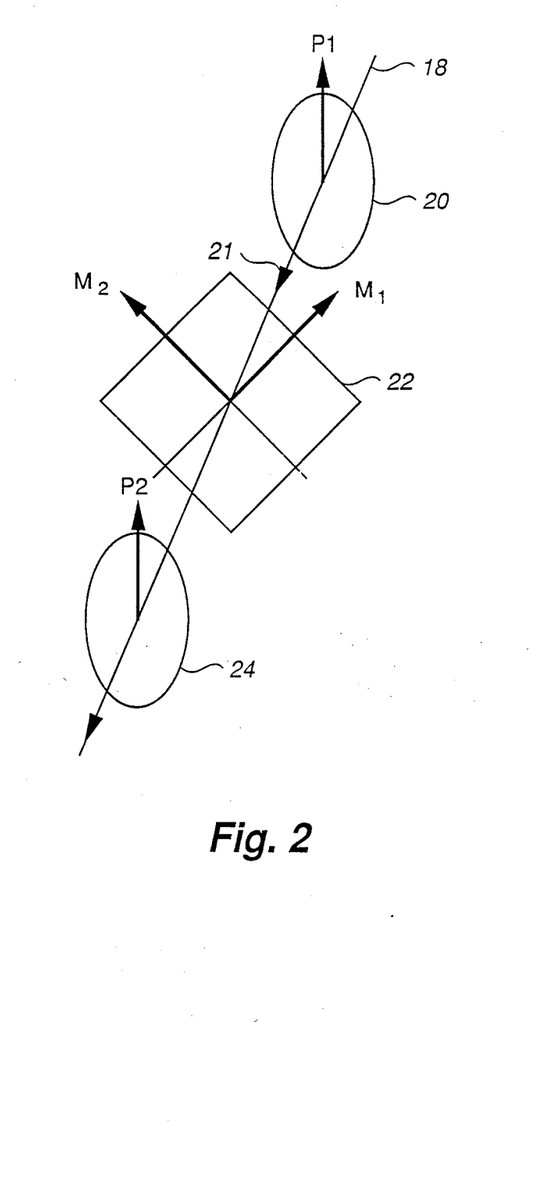
FIG. 2 shows a detailed schematic view of portions of the embodiment of the invention shown in FIG. 1.

Reference is now made to FIG. 2 which shows a detailed schematic view of portions of the embodiment of the invention shown in FIG. 1. The portions shown comprise an interferometer. Birefringent element 22 is disposed between first polarizer 20 and second polarizer 24. The collected fluorescence 18 passes first through first polarizer 20 and the polarized light 21 then enters birefringent element 22. Birefringent element 22 has two principal optical axes, represented by arrows $M_1$ and $M_2$. The electric field of the polarized light 21 is resolved along these optical axes. These optical axes are preferably at 45° relative to the direction of polarization of the first polarizer 20, represented by arrow $P_1$, and of the second polarizer 40, represented by arrow $P_2$. The present invention will work if these optical axes are at any angle other than 0°, 90°, 180° or 270° relative to the direction of polarization of first polarizer 20 and second polarizer 24. $P_1$ and $P_2$ can be parallel to each other, as shown, or they can be perpendicular to each other. Birefringent element 22 has two principal indices of refraction, $n_1$ and $n_2$, corresponding to its two principal optical axes. There is a difference between $n_1$ and $n_2$ and this difference is caused to vary in time by driver 26. Consequently, birefringent element 22 introduces a time-varying phase difference, with an amplitude of at least the wavelength of the fluorescence 18, between the components with polarizations parallel to the optical axes of birefringent element 22. These components see refractive indices $n_1$ and $n_2$ and are the two beams which are mixed after passing through second polarizer 24.

In another embodiment of the invention, still referring to FIG. 2, if the fluorescence 18 is substantially polarized, the interferometer does not include a first polarizer 20. The interferometer only includes a birefringent element 22 and a second polarizer 24.

Still referring to FIG. 2, birefringent element 22 should be driven at a frequency of at least 50 kHz and is preferably driven at a frequency of about 85 kHz. Birefringent element 22 can be a photoelastic modulator, an electrooptic modulator or a magnetooptic modulator. Birefringent element 22 is preferably made of a material capable of induced birefringence. Driver 26, shown in FIG. 1, can be a piezoelectric transducer.

The interferometer shown in FIG. 2 is similar to devices used as light modulators. However, the amplitude of the phase difference introduced in light modulators is typically about one-quarter of a wavelength. The birefringent element 22 of the present invention introduces a phase difference much greater than one-quarter wavelength. The phase difference introduced by birefringent element 22 can be from one to about sixteen times the wavelength of the fluorescence 18. The spectral resolution of the present invention is proportional to the phase difference introduced by birefringent element 22.

Figure 3:
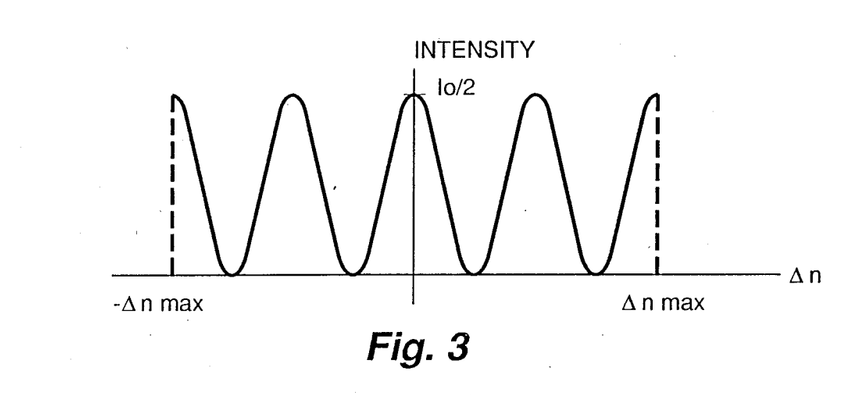
FIGS. 3 and 4 graphically illustrate the output of a detector of the invention as a function of the difference between the refractive indices of the principal axes of the birefringent element used in the interferometer.
Figure 4:
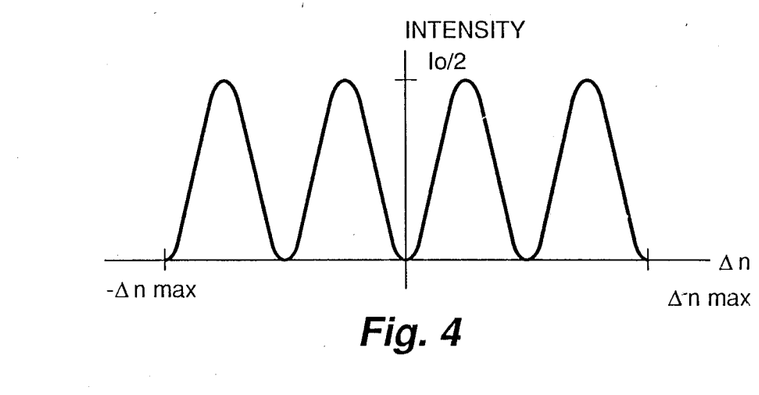

The intensity of the fluorescence waveform leaving second polarizer 24 and detected by first detector 28 varies as a function of the difference ($\Delta n$) between the refractive indices $n_1$ and $n_2$. Assuming that the incoming fluorescence 18 is monochromatic, the intensity of the fluorescence waveform leaving second polarizer 24 varies as a function of $\Delta n$, as shown in FIG. 3. FIGS. 3 and 4 graphically illustrate the output of first detector 28 as a function of $\Delta n$. FIGS. 3 and 4 show that the output of first detector 28 as a function of $\Delta n$ contains a single frequency if the incoming fluorescence 18 is monochromatic and that the frequency of the first detector 28 output is proportional to that of the incoming fluorescence 18. FIG. 4 shows the intensity of the detector 28 output for monochromatic light if first polarizer 20 and second polarizer 24 are crossed. For polychromatic fluorescence 18, the detector 28 output will contain the same spectral components as the incoming fluorescence 18. In FIG. 3, first polarizer 20 and second polarizer 24 are parallel.

Figure 5:
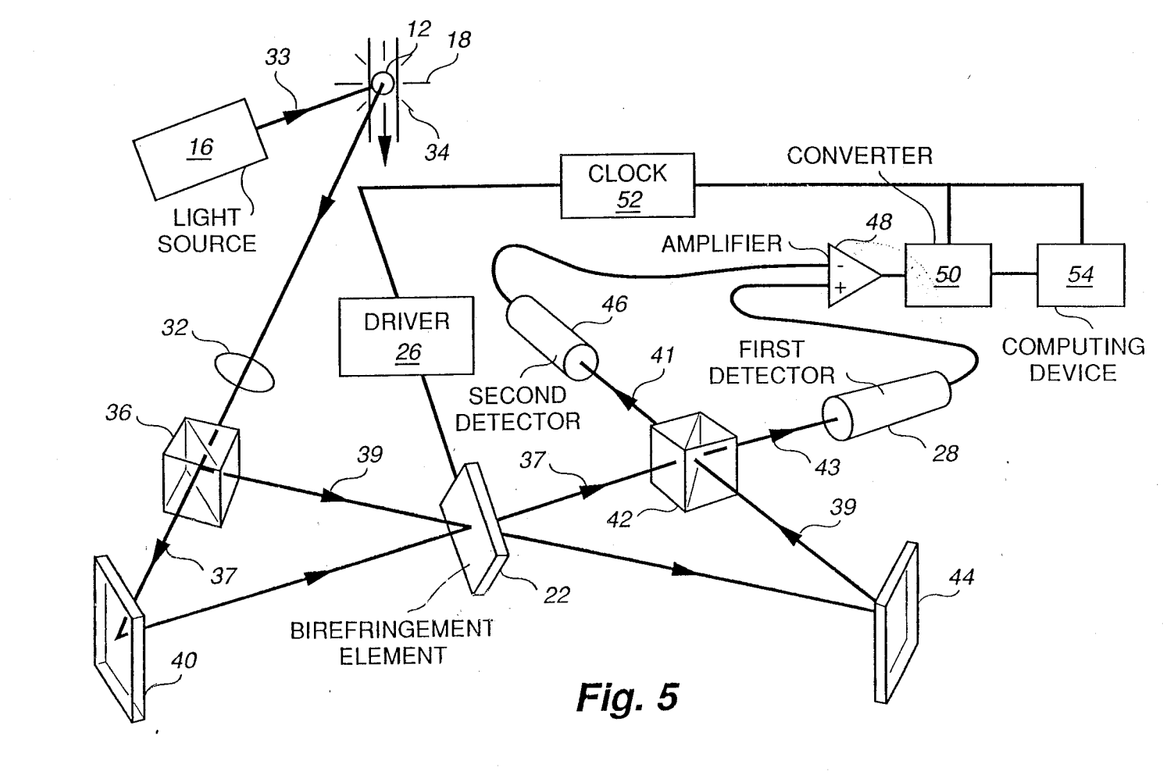
FIG. 5 shows a preferred embodiment of the invention, in partial isometric and partial schematic view.

Reference is now made to FIG. 5 which shows a preferred embodiment of the invention, in partial isometric and in partial schematic view. Light represented by arrow 33 from light source 16 strikes particle 12 producing fluorescence 18 and scattered light represented by arrow 34. The fluorescence 18 passes through first lens 32 and enters a first beam-splitting polarizer 36 which separates the fluorescence 18 into a first plane polarized light wave 37 and a second plane polarized light wave 39. The first light wave 37 is reflected by a first mirror 40 into birefringent element 22, through which it passes before entering a second beam-splitting polarizer 42. Second light wave 39 enters birefringent element 22 at substantially the same location as the point of entry thereinto of first light wave 37. Second light wave 39 is reflected by a second mirror 44 into second polarizer 42. Second light wave 39 is split by second polarizer 42 into a third plane polarized light wave 41 which enters a second detector 46 and a fourth plane polarized light wave 43 which enters first detector 28. First light wave 37 enters second polarizer 42 and is split into a fifth plane polarized light wave, represented by arrow 43, and into a sixth plane polarized light wave, represented by arrow 41. Fifth light wave 43 enters first detector 28 and sixth light wave 41 enters second detector 46. Each detector 28, 46 produces an electrical signal characteristic of the sum of the intensities of the in-phase pair of light waves received by each detector 28, 46. Each light wave has an intensity which depends on the phase difference generated in birefringent element 22. The electrical signal produced by first detector 28 is 180° out of phase with the electrical signal produced by second detector 46.

In this preferred embodiment of the invention, receiving and analyzing system 30 has four components: a differential amplifier 48, an analog-to-digital converter 50, a clock 52 and a computing device 54. Differential amplifier 48 produces a signal representing the difference between the electrical signals generated by first detector 28 and second detector 46. Amplifier 48 is connected to first detector 28 and second detector 46. Amplifier 48 is connected to converter 50 which digitizes the electrical signals. A clock 52 is operatively connected to converter 50 and through driver 26 to birefringent element 22. The clock 52 and birefringent element 22 are phase-locked. Clock 52 strobes converter 50 at a frequency which is greater than the frequency at which the birefringent element 22 is driven. Computing device 54 is operatively connected to converter 50 and to clock 52. Computing device 54 computes, stores, combines, and outputs the numbers representing the intensity of each of the spectral wavelengths of the collected fluorescence 18.

Figure 6:
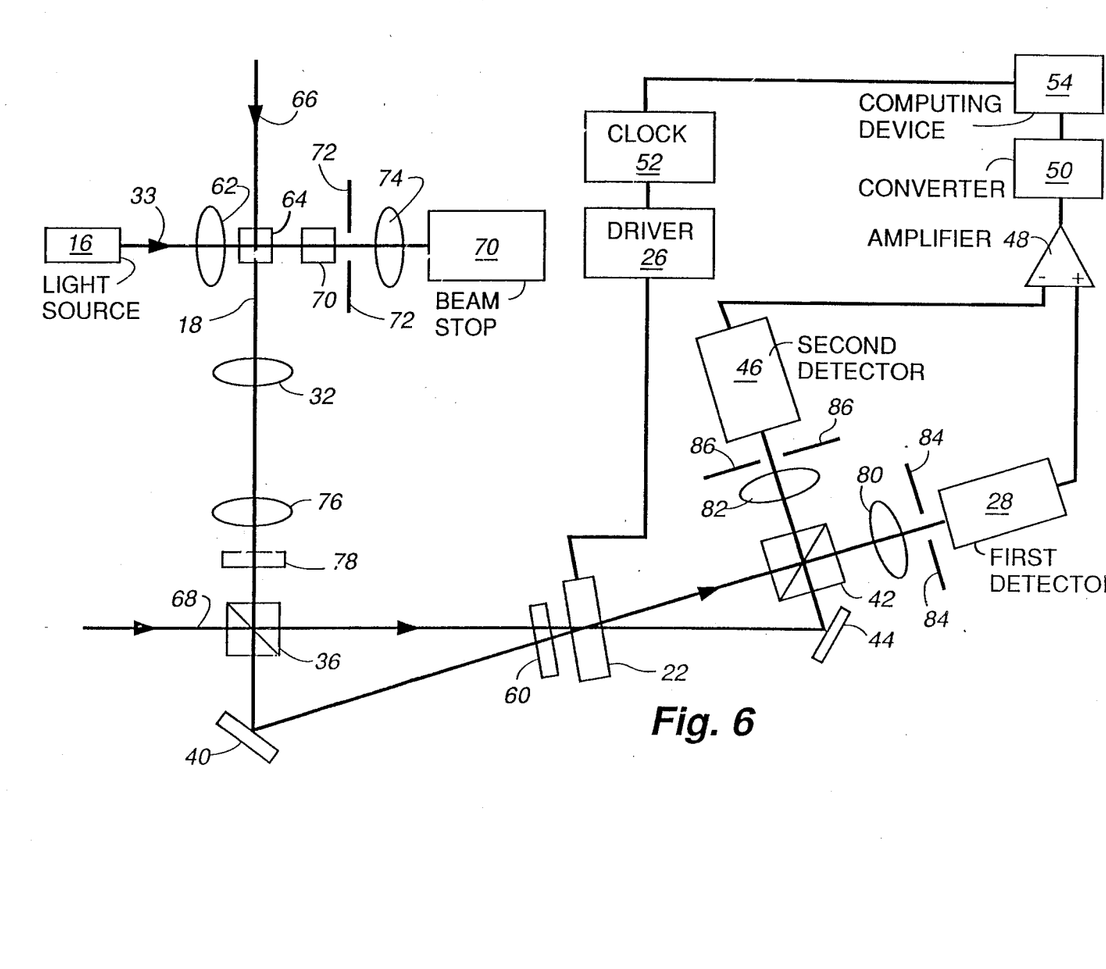
FIG. 6 shows a schematic view of an embodiment of the invention having elements additional to the embodiment shown in FIG. 5.

Reference is now made to FIG. 6 which shows a schematic view of an embodiment of the invention having all of the elements described in FIG. 5 and additional elements. The common elements have the same reference numerals in both figures. This embodiment of the invention further includes a birefringent compensator 60 located between birefringent element 22 and first polarizer 36. Compensator 60 can be located anywhere between first polarizer 36 and second polarizer 42 in such a manner that both the first and second waves pass therethrough. The optical axes of compensator 60 are parallel to the optical axes of birefringent element 22. Compensator 60 increases the spectral resolution of the apparatus by introducing an additional phase difference in the polarized light 21, shown in FIG. 1. As already mentioned, the spectral resolution of the apparatus is proportional to the phase-modulation amplitude. The phase-modulation amplitude determines the range of the Fourier transform of the spectrum which can be sampled. As the phase difference introduced by birefringent element 22 oscillates harmonically about zero, the outputs of first detector 28 and second detector 46 contain two symmetrical regions of the Fourier transform with a range proportional to the phase-shift amplitude. The resolution of the apparatus can be doubled by eliminating this redundancy. This increase is achieved by using compensator 60 to introduce a fixed phase shift in the polarized light 21 equal to the maximum phase shift introduced by birefringent element 22.

The embodiment of the invention shown in FIG. 6 may also include a second lens 62 through which the light represented by arrow 33 from light source 16 passes before exciting particles 12 (not shown). The particles 12 pass through a flow chamber 64 which is a component of flow cytometer 10, shown in FIG. 1. A first reference beam, represented by arrow 66, and a second reference beam, represented by arrow 68, are used to align the elements of the apparatus and for wavelength calibration. The apparatus can further include a beam stop 70, an aperture defined by plate 72, a third lens 74 and a forward light scatter detector 76. Fluorescence 18 passes through first lens 32 and, before entering first polarizer 36, passes through a fourth lens 76 and a filter 78. The polarized fluorescence which exits second polarizer 42 has two components, one of which passes through a fifth lens 80 and the other passes through a sixth lens 82. These components then pass through a second aperture formed by plate 84 and a third aperture formed by plate 86 before reaching first detector 28 and second detector 54, respectively.

Figure 7:
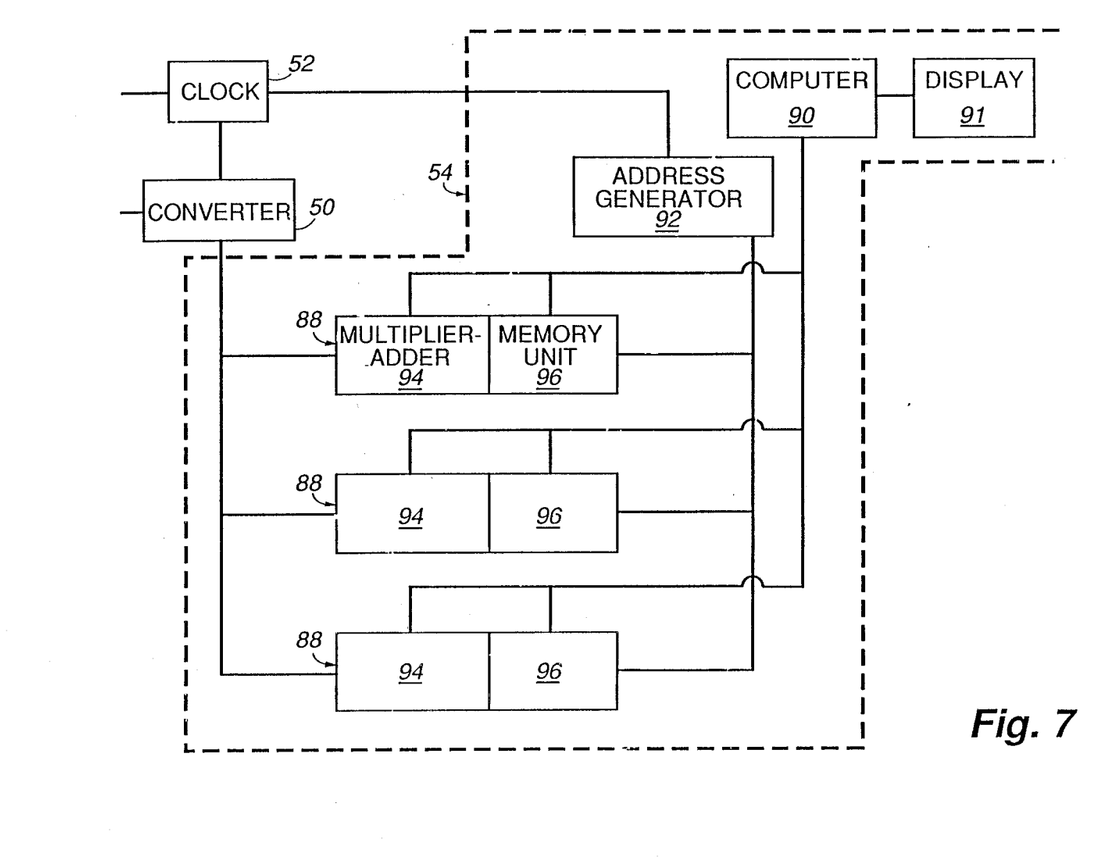
FIG. 7 shows a schematic view of the computing device used in a preferred embodiment of the invention.

Reference is now made to FIG. 7 which shows a schematic view of the computing device 54 used in a preferred embodiment of the invention. The computing device 54 is connected to clock 52 and converter 50. Computing device 54 includes a multiplicity of microprocessors 88, only three of which are shown. The number of microprocessors 88 equals the number of spectral channels over which the apparatus can measure fluorescence 18. In a preferred embodiment of the invention there are thirty-two microprocessors 88 and thirty-two spectral channels. Three microprocessors 88 are shown for convenience. Each microprocessor 88 computes, stores, and outputs a single number representing the intensity of one spectral channel, or wavelength, of the collected fluorescence 18. Each microprocessor 88 is connected to converter 50 and to clock 52. This preferred embodiment of the invention also includes a computer 90 for combining and storing the numbers, representing the intensity of the spectral channels of the collected fluorescence 18, calculated by the microprocessors 88. Computer 90 is connected to each of the microprocessors 88. Computer 90 can be connected to a display device 91 for displaying the numbers representing the intensity of the spectral channels.

The apparatus can also include an address generator 92. Address generator 92 is connected to clock 52 and to each of the microprocessors 88 and provides each of the microprocessors 88 with a coefficient index and address to correlate the coefficients used by each of the microprocessors 88 to the digital signal transmitted by converter 50.

Each microprocessor 88 can include a multiplier-adder 94. Each multiplier-adder 94 computes a single number representing the intensity of one spectral channel of the collected fluorescence 18. Each multiplier-adder 94 is connected to converter 50 and can be a single chip. Each microprocessor 88 can include a random access memory unit 96 for storing coefficients used by the multiplier-adders 94. Each random access memory unit 96 is connected to computer 90 and to a separate multiplier-adder 94.

Computer 90 can control the spectral response of each of the microprocessors 88. The random access memory units 96 contain the coefficients for the transformation and can be entered by computer 90. As a consequence, the spectral characteristic of each channel can be modified within the spectral resolution of the apparatus. Thus, each data processing channel can be made to represent one spectral band in which case each channel represents one region of the emission spectrum, and the whole spectrum can be acquired for each individual particle 12 if the computing device 54 has the required number of spectral channels. Alternatively, a more general spectral characteristic can be programmed into each channel, so that the response of each channel can be optimized for one particular fluorochrome. This is superior to the conventional broadband spectral analysis in flow cytometry. For a given set of fluorochromes, the optimum spectral characteristics can be programmed into each channel, thus providing the best separation of the fluorochromes. The present invention is very useful in flow cytometry because it is able to process the detected waveform in a time shorter than the average interval between the excitation of successive particles 12 by light source 16.

Each multiplier-adder 94 computes one point of the spectrum. Each random access memory unit 96 stores the coefficient of the transformation for one spectral channel as a particle 12 leaves the light beam 33, shown in FIG. 5. Each multiplier-adder 94 accumulates one element of the spectrum. Thus, the transformed spectral information is available within the time required for one digital conversion, one multiplication and one addition after particle 12 leaves light beam 33. In the apparatus of the present invention, this processing delay is on the order of 150 ns.

Figure 8:
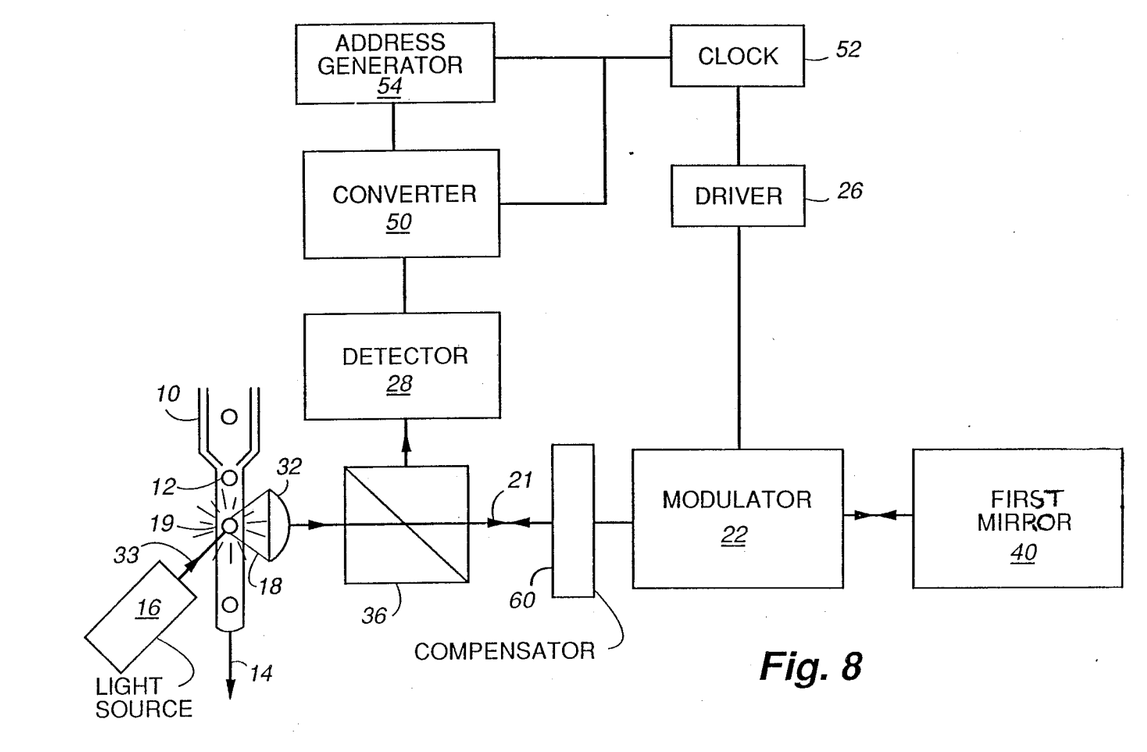
FIG. 8 shows a schematic view of an embodiment of the invention having a single polarizer and a mirror for reflecting light back through the birefringent element and polarizer.

Reference is now made to FIG. 8 which shows a schematic view of another embodiment of the invention, which is an apparatus for simultaneously measuring a plurality of spectral wavelengths present in fluorescence 18 produced when a light source 16 excites individual particles 12 moving sequentially through the fluorescence excitation region 19 of a flow cytometer 10. The apparatus includes a first beam-splitting polarizer 36 for receiving fluorescent light 18 and for defining a first direction for the electric field of the polarized light 21 which passes through first polarizer 36. A modulatable birefringent element 22 receives the polarized light 21 from first polarizer 20. Birefringent element 22 has first and second optical axes, shown in FIG. 2, along which the electric field of the polarized light 21 is resolved into two components. The light wave corresponding to each of the resolved electric field components travels at a different velocity, so two light waves, having different electric field directions and a shift in phase greater than approximately one wavelength of the longest wavelength component of the fluorescent light 18, emerge from birefringent element 22.

A first lens 32 collects the fluorescence 18 and directs it towards first polarizer 36. First lens 32 is located between first polarizer 36 and flow cytometer 10. The optical axes of birefringent element 22 can be at any angle other than 0°, 90°, 180° or 270° relative to the direction of polarization of first polarizer 36. First polarizer 36 is located between lens 26 and birefringent element 22. Birefringent element 22 is driven at a sufficiently high frequency by a driver 26 to allow spectral data acquisition during the time period when a particle 12 travels through excitation region 19. A compensator 60 for increasing the spectral resolution of the apparatus can be located between first polarizer 36 and birefringent element 22. A first mirror 40 is located opposite of birefringent element 22 from first polarizer 36. First mirror 40 reflects the two phase-shifted light waves emerging from birefringent element 22 back through birefringent element 22, increasing their phase shift, and into first polarizer 36, which resolves their electric fields along the initial electric field direction, so that the two doubly phase-shifted light waves emerge plane polarized with the same direction of polarization and at an angle to the fluorescence 18 incident on first polarizer 36. A first detector 28 receives these doubly phase-shifted light waves emerging from first polarizer 36 and interacts therewith to produce an electrical signal characteristic of the interference pattern generated as a result of the first polarizer 36 resolving the electric fields of the two doubly phase-shifted light waves along the initial electric field direction. The converter 50, clock 52 and computing device 54 shown in FIG. 8 operate in the same manner as the corresponding elements shown in FIG. 5.

Figure 9:
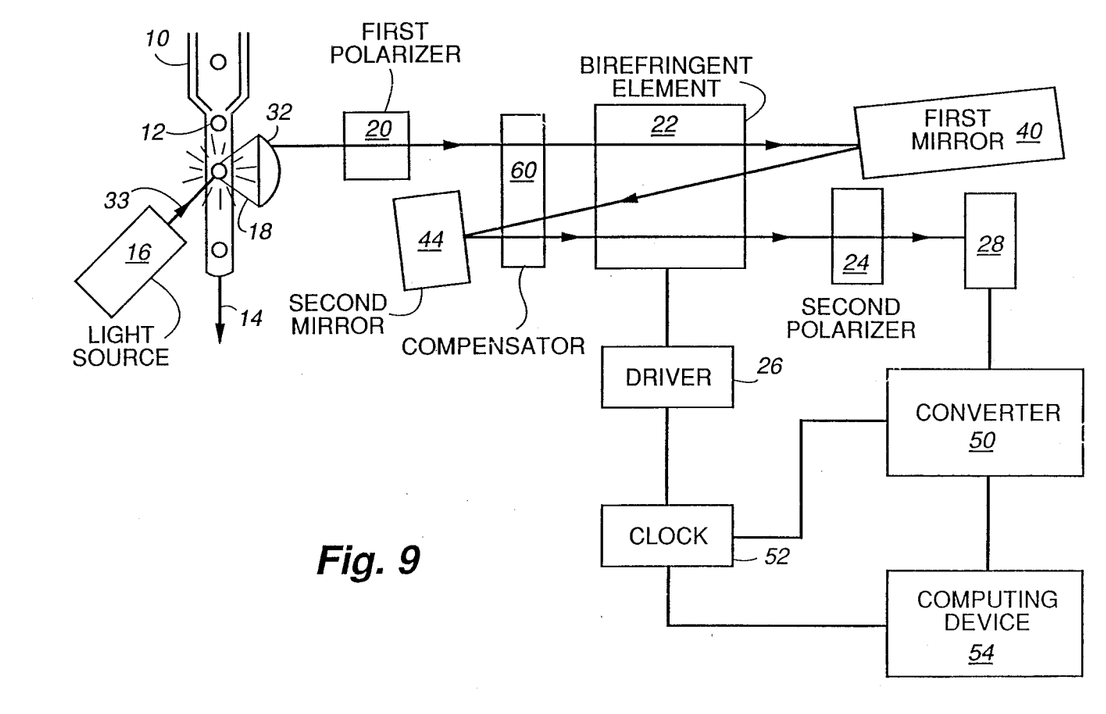
FIG. 9 shows a schematic view of an embodiment of the invention that uses mirrors to reflect light through the birefringent element.

Reference is now made to FIG. 9 which shows a schematic view of another embodiment of the invention. This embodiment of the invention is similar to the embodiment of the invention shown in FIG. 8. In FIG. 9, fluorescence 18 passes through first polarizer 20, compensator 60 and birefringent element 22 and is then reflected by first mirror 40 back through birefringent element 22 and compensator 60. Second mirror 44 reflects the polarized light waves through compensator 60 and birefringent element 22, and into second polarizer 24. The phase shift of the polarized light waves and spectral resolution of the apparatus is increased by each additional pass through birefringent element 22 and compensator 60.

The spectral resolution of each apparatus of the present invention is proportional to the phase-modulation amplitude, or phase difference introduced. The resolution is also affected by the noise level, the signal-to-noise ratio and by how well the collected fluorescence 18 is collimated. A formula relating the depth of modulation to the resolution of the apparatus is as follows:

$$\delta\omega = \frac{2\omega_o}{\pi} \frac{1}{n}$$

where $\delta\omega$ is basically the full-width-at-half-maximum of the angular frequency of the electromagnetic radiation ($\omega = 2\pi c/\lambda$, where $\lambda$ is the wavelength of the radiation), $\omega_o$ is the center frequency of the radiation and n is the number of waves swept through by the birefringent element 22. The resolution for n = 16 (with the birefringent compensator 60 in place) is 10 nm at 500 nm in wavelength units.

It was found experimentally that a typical fluorescence signal from a laser-excited particle moving through a flow cytometer, has a usable fluoroscence duration of approximately 150 μs. With the modulatable birefringent element operating at about 85 kHz, it takes about 3 μs for an interferogram which represents a scan of 8 waves. Therefore, approximately 50 interferograms may be averaged. With the birefringent compensator in place, a scan of 16 waves is accomplished in about 6 μs which means that one may average about 25 interferograms with a resolution of approximately 10 nm at 500 nm. Experiments designed to establish the sensitivity of the apparatus of the present invention have been performed. Spectral analysis and real-time fluorochrome separation on polystyrene microspheres labeled with $10^6$ fluorescein isothiocyanate and propidium iodide soluble molecule equivalents (Flow Cytometry Standards, Research Triangle Park, NC) using an excitation beam power of 150 mW at 488 nm have been achieved. Moreover, it was also found that the fluorescein fluorescence can be separated from water Raman scattering background using microspheres labeled with only $5 \times 10^4$ fluorescein isothiocyanate soluble molecule equivalents which appears to be the sensitivity limit of the apparatus of our invention in its current state of development.

Those skilled in the art will appreciate that a plurality of spectral wavelengths present in electromagnetic radiation other than fluorescence can be simultaneously measured with the embodiments of the present invention. Visible, ultraviolet and ir radiation can be used with the present invention. The compensator 60 and birefrigent element 22 can be made of fused silica for ultraviolet or visible radiation and they can be made of zinc selenide for ir and the longer wavelengths of visible radiation.

The foregoing description of several embodiments of the invention has been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for simultaneously measuring a plurality of spectral wavelengths present in fluorescence, the apparatus comprising in combination:
   a. a first polarizer for receiving the fluorescence having an electric field disposed in an arbitrary direction and for defining a first direction for the electric field of the fluorescence transmitted therethrough;
   b. modulatable birefringent means for receiving the transmitted polarized light from said first polarizer, said birefringent means having first and second optical axes along which the electric field of the transmitted polarized light is resolved into two components, the light wave corresponding to each of the resolved electric field components traveling at a different velocity, so that two first light waves emerge from said birefringent means having different electric field directions and a shift in phase greater than one wavelength of the longest wavelength component of the fluorescence;
   c. a second polarizer for receiving the two first light waves emerging from said birefringent means and resolving their electric fields along a second direction, so that two second light waves emerge plane polarized and with the same direction of polarization;
   d. means for modulating said birefringent means such that resolution suitable for measurement of the plurality of spectral wavelengths is achieved;
   e. first detector means for receiving the two second light waves emerging from said second polarizer and interacting therewith to produce an electrical signal characteristic of the interference pattern generated as a result of the interference of the two second light waves having different phase; and
   f. means for receiving the electrical signal from said first detector means and for separating the signal into its spectral components.

2. The apparatus as described in claim 1, further comprising first reflecting means, second reflecting means and second detection means, wherein said first polarizer comprises a beam-splitting polarizer for separating the fluorescence into a first plane polarized light wave traveling in a parallel direction to the fluorescence incident thereon and a second plane polarized light wave traveling at an angle thereto, the second polarized light wave entering said birefringent means after exiting said first beam-splitting polarizer, the first polarized light wave being reflected into said birefringent means by said first reflecting means at the same location as the point of entry thereinto of the second polarized light wave, the second polarized light wave being reflected into said second beam-splitting polarizer by said second reflecting means after exiting said birefringent means, said second polarized light wave being split by said second beam-splitting polarizer into a third plane polarized light wave and a fourth plane polarized light wave, the third polarized light wave continuing along the path of entry thereof into said second beam-splitting polarizer into said second detection means and the fourth polarized light wave exiting from said second beam-splitting polarizer at an angle to the third polarized light wave and entering said first detection means, the first polarized light wave entering said second beam-splitting polarizer after exiting said birefringent means and being split into a fifth plane polarized light wave and a sixth plane polarized light wave, the fifth polarized light wave traveling along the path of entry thereof into said second beam-splitting polarizer and entering said first detection means after exiting said second beam-splitting polarizer and the sixth polarized light wave exiting said second beam-splitting polarizer at an angle to the fifth light wave and entering said second detection means, said first detection means interacting with the fourth polarized light wave and the fifth polarized light wave to produce an electrical signal characteristic of the sum of the intensities of the in-phase pairs of light waves received by said first detection means, the light waves comprising each pair having a phase difference generated in said birefringent means, said second detection means interacting with the third polarized light wave and the sixth polarized light wave to produce an electrical signal characteristic of the sum of the intensities of the in-phase pairs of light waves received by said second detection means, the light waves comprising each pair having a phase difference generated in said birefringent means, the electrical signal produced in said first detection means being 180° out of phase with the electrical signal produced in said second detection means, and wherein said receiving and analyzing means receives and quantitatively separates into their spectral components the signals from both said first detection means and said second detection means, whereby all of the fluorescence is utilized.

3. The apparatus as described in claim 1 or 2, further comprising a birefringent compensator for intercepting the polarized light exiting said first polarizer before it enters said second polarizer and introducing a fixed phase shift therein of the same magnitude as the phase shift introduced therein by said birefringent means, said birefringent compensator having first and second optical axes parallel to the optical axes of said birefringent means, whereby the spectral resolution of the apparatus is doubled.

4. The apparatus as described in claim 3, wherein the first direction of the electric field is parallel to the second direction of the electric field.

5. The apparatus as described in claim 1 or 2 wherein a lens is interposed between the fluorescence and said first polarizer for collecting the fluorescence and directing the collected fluorescence into said first polarizer.

6. The apparatus of claim 1 wherein said receiving and analyzing means comprises an analog-to-digital converter for digitizing the electrical signal, said converter being operatively connected to said first detector means, a clock connected to said converter and to said modulation means, said clock and said modulation means being phase-locked, and computing means for computing, storing, combining and outputting the numbers representing the intensity of each spectral component of the fluorescence, said computing means being operatively connected to said converter and to said clock.

7. The apparatus of claim 6 wherein said computing means includes a multiplicity of microprocessors each for computing, storing and outputting a single number representing the intensity of one spectral component of the collected fluorescence, each of said microprocessors being connected to said converter and to said clock, and a computer for combining and storing the numbers, representing the intensity of the spectral components of the collected fluorescence, calculated by said microprocessors, said computer being connected to each of said microprocessors.

8. The apparatus of claim 7 further comprising an address generator connected to said clock and to each of said microprocessors for providing each of said microprocessors with a coefficient index address to correlate the coefficients used by each of said microprocessors to the digitized signal transmitted by said converter.

9. The apparatus of claim 6 wherein said computer controls the spectral response of each of said microprocessors.

10. The apparatus of claim 1 wherein said birefringent means is driven by said modulation means at a frequency of at least 50 kHz.

11. The apparatus of claim 1 wherein said birefringent means introduces a phase shift of between two and sixteen times the wavelength of the fluorescence.

12. The apparatus of claim 1 wherein the optical axes of said birefringent means are at an angle of 45° relative to the direction of polarization of said first and second polarizers.

13. The apparatus of claim 1 wherein the optical axes of said birefringent means are at an angle of 135°, 225° or 315° relative to the direction of polarization of said first and second polarizers.

14. An apparatus for simultaneously measuring a plurality of spectral wavelengths present in polarized fluorescence, the apparatus comprising in combination:
  a. modulatable birefringent means for receiving substantially polarized fluorescence having an electric field disposed in a particular direction, said birefringent means having first and second optical axes along which the electric field of the fluorescence is resolved into two components, the light wave corresponding to each of the resolved electric field components traveling at a different velocity, so that two first light waves emerge from said birefringent means having different electric field directions and a shift in phase greater than one wavelength of the longest wavelength component of the fluorescence;

15. The apparatus as described in claim 14, further comprising a birefringent compensator for intercepting the fluorescence before it enters said polarizer and introducing a fixed phase shift therein of the same magnitude as the phase shift introduced therein by said birefringent means, said birefringent compensator having optical axes parallel to the optical axes of said birefringent means, whereby the spectral resolution doubled.

16. The apparatus as described in claim 14 or 15 wherein a lens is interposed between fluorescence and said birefringent means for collecting the fluorescence and directing the collected fluorescent light into said birefringent means.

17. An apparatus for simultaneously measuring a plurality of spectral wavelengths present in electromagnetic radiation from a source thereof, the apparatus comprising in combination:
  a. a first polarizer for receiving electromagnetic radiation having an electric field disposed in an arbitrary direction, and for defining a first direction for the electric field of the electromagnetic radiation transmitted therethrough;
  b. modulatable birefringent means for receiving the transmitted polarized electromagnetic radiation from said first polarizer, said birefringent means having first and second optical axes along which the electric field of the transmitted polarized electromagnetic radiation is resolved into two components, the light wave corresponding to each of the resolved electric field components traveling at a different velocity, so that two first light waves emerge from said birefringent means having different electric field directions and a shift in phase greater than one wavelength of the longest wavelength component of the electromagnetic radiation;
  c. a second polarizer for receiving the two first light waves emerging from said birefringent means and resolving their electric fields along a second direction, so that two second light waves emerge plane polarized and with the same direction of polarization;
  d. means for modulating said birefringent means such that resolution suitable for measurement of the plurality of spectral wavelengths results during the time period of occurrence of the electromagnetic radiation;

e. first detector means for receiving the two second light waves emerging from said second polarizer and interacting therewith to produce an electrical signal characteristic of the interference pattern generated as a result of the interference of the two second light waves having different phase; and f. means for receiving the electrical signal from said first detector means and for separating the signal into its spectral components.

18. The apparatus as described in claim 17, further comprising first reflecting means, second reflecting means and second detection means, wherein said first polarizer comprises a beam-splitting polarizer for separating the incident electromagnetic radiation into a first plane polarized light wave traveling in a parallel direction to the electromagnetic radiation incident thereon and a second plane polarized light wave traveling at an angle thereto, the second polarized light wave entering said birefringent means after exiting said first beam-splitting polarizer, the first polarized light wave being reflected into said birefringent means by said first reflecting means at the same location as the point of entry thereinto of the second polarized light wave, the second polarized light wave being reflected into said second beam-splitting polarizer by said second reflecting means after exiting said birefringent means, said second polarized light wave being split by said second beam-splitting polarizer into a third plane polarized light wave and a fourth plane polarized light wave, the third polarized light wave continuing along the path of entry into said second beam-splitting polarizer into said second detection means and the fourth polarized light wave exiting from said second beam-splitting polarizer at an angle to the third polarized light wave and entering said first detection means, the first polarized light wave entering said second beam-splitting polarizer after exiting said birefringent means and being split into a fifth plane polarized light wave and a sixth plane polarized light wave, the fifth polarized light wave traveling along the path of entry thereof into said second beam-splitting polarizer and entering said first detection means after exiting said second beam-splitting polarizer and the sixth polarized light wave exiting said second beam-splitting polarizer at an angle to the fifth polarized light wave and entering said second detection means, said first detection means interacting with the fourth polarized light wave and the fifth polarized light wave to produce an electrical signal characteristic of the sum of the intensities of the in-phase pairs of light waves received by said first detection means, the light waves comprising each pair having a phase difference generated in said birefringent means, said second detection means interacting with the third polarized light wave and the sixth polarized light wave to produce an electrical signal characteristic of the sum of the intensities of the in-phase pairs of light waves received by said second detection means, the light waves comprising each pair having a phase difference generated in said birefringent means, the electrical signal produced in said first detection means being 180° out of phase with the electrical signal produced in said second detection means, and wherein said means for receiving the electrical signal receives and quantitatively analyzes into their spectral components the signals from both said first detection means and said second detection means, whereby all of the electromagnetic radiation is utilized.

19. The apparatus as described in claim 17 or 18, further comprising a birefringent compensator for intercepting the polarized electromagnetic radiation exiting said first polarizer before it enters said second polarizer and introducing a fixed phase shift therein of the same magnitude as the phase shift introduced therein by said birefringent means, said birefringent compensator having optical axes parallel to the optical axes of said birefringent means, whereby the spectral resolution is doubled.

20. The apparatus as described in claim 19, wherein the first direction for the electric field is parallel to the second direction for the electric field.

21. The apparatus as described in claim 17 or 18 wherein a lens is interposed between the source of the electromagnetic radiation and said first polarizer for collecting the electromagnetic radiation and directing the collected electromagnetic radiation into said first polarizer.

22. An apparatus for simultaneously measuring a plurality of spectral wavelengths present in polarized electromagnetic radiation from a source thereof, the apparatus comprising in combination:

a. modulatable birefringent means for receiving the polarized electromagnetic radiation, having an electric field disposed in a particular direction, said birefringent means having first and second optical axes along which the electric field of the polarized electromagnetic radiation is resolved into two components, the light wave corresponding to each of the resolved electric field components traveling at a different velocity, so that two first light waves emerge from said birefringent means having different electric field directions and a shift in phase greater than one wavelength of the longest wavelength component of the electromagnetic radiation;

b. a polarizer for receiving the two first light waves emerging from said birefringent means and resolving their electric fields along a second direction, so that two second light waves emerge plane polarized and with the same direction of polarization;

c. means for modulating said birefringent means such that resolution suitable for measurement of the plurality of spectral wavelengths results during the time period of occurrence of the electromagnetic radiation;

d. detector means for receiving the two second light waves emerging from said polarizer and interacting therewith to produce an electrical signal characteristic of the interference pattern generated as a result of the interference of the two second light waves having different phase; and e. means for receiving the electrical signal from said detector means and for separating the signal into its spectral components.

23. The apparatus as described in claim 22, further comprising a birefringent compensator for intercepting the polarized electromagnetic radiation before it enters said polarizer and introducing a fixed phase shift therein of the same magnitude as the phase shift introduced therein by said birefringent means, said birefringent compensator having optical axes parallel to the optical axes of said birefringent means, whereby the spectral resolution of the apparatus is doubled.

24. The apparatus as described in claim 22 or 23, wherein a lens is interposed between the source of polarized electromagnetic radiation and said polarizer for collecting the electromagnetic radiation and directing the collected electromagnetic radiation into said polarizer.

25. An apparatus for simultaneously measuring a plurality of spectral wavelengths present in fluorescence, the apparatus comprising in combination:
   a. a beam-splitting polarizer for receiving the fluorescence having an electric field disposed in an arbitrary direction and for defining an initial direction for the electric field of the fluorescence transmitted therethrough;
   b. modulatable birefringent means for receiving the transmitted polarized light from said polarizer, said birefringent means having first and second optical axes along which the electric field of the transmitted polarized light is resolved into two components, the light wave corresponding to each of the resolved electric field components traveling at a different velocity, so that two first light waves emerge from said birefringent means having different electric field directions and a shift in phase greater than one wavelength of the longest wavelength component of the fluorescence;
   c. means for modulating said birefringent means such that resolution suitable for measurement of the plurality of spectral wavelengths is achieved;
   d. reflecting means for reflecting the two first phase-shifted light waves emerging from said birefringent means back therethrough along the path of first entry thereof and in the opposite direction, so that the phase shift therebetween is increased, said polarizer receiving the two doubly phase-shifted light waves, each having an electric field, and resolving the electric fields thereof along the initial electric field direction, so that two second phase-shifted light waves emerge plane polarized with the same direction of polarization and travel at an angle to the fluorescence incident on said polarizer;
   e. detector means for receiving the two second light waves emerging from said polarizer and interacting therewith to produce an electrical signal characteristic of the interference pattern generated as a result of the interference of the two second light waves having different phase; and
   f. means for receiving the electrical signal from said detector means and for separating the signal into its spectral components.

26. An apparatus for simultaneously measuring a plurality of spectral wavelengths present in electromagnetic radiation from a source thereof, the apparatus comprising in combination:
   a. a beam-splitting polarizer for receiving electromagnetic radiation having an electric field disposed in an arbitrary direction and for defining an initial direction for the electric field of the electromagnetic radiation transmitted therethrough;
   b. modulatable birefringent means for receiving the transmitted polarized light from said polarizer, said birefringent means having first and second optical axes along which the electric field of the transmitted polarized light is resolved into two components, the light wave corresponding to each of the resolved electric field components traveling at a different velocity, so that two first light waves emerge from said birefringent means having different electric field directions and a shift in phase greater than one wavelength of the longest wavelength component of the fluorescent light;
   c. means for modulating said birefringent means such that resolution suitable for measurement of the plurality of spectral wavelengths results during the time period of occurrence of the electromagnetic radiation;
   d. reflecting means for reflecting the two first phase-shifted light waves emerging from said birefringent means back therethrough along the path of first entry thereof and in the opposite direction, so that the phase shift therebetween is increased, said polarizer receiving the two doubly phase-shifted light waves, each having an electric field, and resolving the electric fields thereof along the initial electric field direction, so that two second phase-shifted light waves emerge plane polarized with the same direction of polarization and travel at an angle to the electromagnetic radiation incident on said polarizer;
   e. detector means for receiving the two second light waves emerging from said polarizer and interacting therewith to produce an electrical signal characteristic of the interference pattern generated as a result of the interference of the two second light waves having different phase; and
   f. means for receiving the electrical signal from said detector means and for separating the signal into its spectral components.

27. An apparatus for simultaneously measuring a plurality of spectral wavelengths present in fluorescence, the apparatus comprising in combination:
   a. a first polarizer for receiving the fluorescence having an electric field disposed in an arbitrary direction, and for defining a first direction for the electric field of the fluorescence transmitted therethrough;
   b. modulatable birefringent means for receiving the transmitted polarized light from said first polarizer, said birefringent means having first and second optical axes along which the electric field of the transmitted polarized light is resolved into two components, the light wave corresponding to each of the resolved electric field components traveling at a different velocity, so that two first light waves emerge from said birefringent means having different electric field directions and a shift in phase greater than one wavelength of the longest wavelength component of the fluorescent light;
   c. means for modulating said birefringent means such that resolution suitable for measurement of the plurality of spectral wavelengths is achieved;
   d. first reflecting means for reflecting the two first phase-shifted light waves emerging from said birefringent means back therethrough, so that the phase shift between the two light waves is increased;
   e. second reflecting means for receiving the two doubly phase-shifted first light waves emerging from said modulatable birefringent means and reflecting the two doubly phase-shifted first light waves back through said modulatable birefringent means, so that an additional phase shift is introduced between the two doubly phase-shifted first light waves;
   f. a second polarizer for receiving the two triply phase-shifted first light waves emerging from said birefringent means, each having an electric field, and resolving their electric fields along a second direction, so that two second light waves emerge plane polarized and with the same direction of polarization;

g. detector means for receiving the light waves emerging from said second polarizer and interacting therewith to produce an electrical signal characteristic of the interference pattern generated as a result of the interference of the two second light waves having different phase; and h. means for receiving the electrical signal from said detector means and for separating the signal into its spectral components.

28. The apparatus as described in claim 27, wherein the first direction of the electric field is parallel to the second direction of the electric field.

29. The apparatus as described in claim 27 or 28 further comprising a birefringent compensator disposed between said first reflecting means and said second reflecting means, said birefringent compensator having third and fourth optical axes parallel to the optical axes of said birefringent means and introducing a fixed phase shift in the light passing therethrough so that the spectral resolution of said apparatus is doubled by each pass of the light through said birefringent compensator.

30. An apparatus for simultaneously measuring a plurality of spectral wavelengths present in electromagnetic radiation from a source thereof, the apparatus comprising in combination:
a. a first polarizer for receiving the electromagnetic radiation having an electric field disposed in an arbitrary direction, and for defining a first direction for the electric field of the electromagnetic radiation transmitted therethrough;
b. modulatable birefringent means for receiving the transmitted polarized light from said first polarizer, said birefringent means having first and second optical axes along which the electric field of the transmitted polarized light is resolved into two components, the light wave corresponding to each of the resolved electric field components traveling at a different velocity, so that two first light waves emerge from said birefringent means having different electric field directions and a shift in phase greater than one wavelength of the longest wavelength component of the electromagnetic radiation;
c. means for modulating said birefringent means such that resolution suitable for measurement of the plurality of spectral wavelengths results during the time period of occurrence of the electromagnetic radiation;
d. first reflecting means for reflecting the two phase-shifted first light waves emerging from said birefringent means back therethrough, so that the phase shift between the two light waves is increased;
e. second reflecting means for receiving the two doubly phase-shifted first light waves emerging from said birefringent means and reflecting the two doubly phase-shifted light waves back through said birefringent means, so that an additional phase shift is introduced between the two doubly phase-shifted first light waves;
f. a second polarizer for receiving the two triply phase-shifted first light waves emerging from said birefringent means, each having an electric field, and resolving their electric fields along a second direction, so that two second light waves emerge plane polarized and with the same direction of polarization;
g. detector means for receiving the light waves emerging from said second polarizer and interacting therewith to produce an electrical signal characteristic of the interference pattern generated as a result of the interference of the two second light waves having different phase; and
h. means for receiving the electrical signal from said detector means and for separating the signal into its spectral components.

31. The apparatus as described in claim 30, further comprising a birefringent compensator disposed between said first reflecting means and said second reflecting means, said birefringent compensator having third and fourth optical axes parallel to the optical axes of said birefringent means and introducing a fixed phase shift in the light passing therethrough so that the spectral resolution of said apparatus is doubled by each pass of the light through said birefringent compensator.

32. The apparatus as described in claim 31, wherein the first direction of the electric field is parallel to the second direction of the electric field.

33. A method for simultaneously measuring a plurality of spectral wavelengths present in electromagnetic radiation from a source thereof comprising the steps of:
a. linearly polarizing the electromagnetic radiation having an electric field disposed in an arbitrary direction along a first direction;
b. resolving the electric field of the linearly polarized electromagnetic radiation along two substantially orthogonal directions;
c. introducing a phase shift of greater than one wavelength of the longest wavelength component of the electromagnetic radiation between light waves associated with each of the resolved electric fields;
d. linearly polarizing the phase-shifted light waves along a second direction;
e. detecting the interference pattern generated from the interaction of the linearly polarized, phase shifted light waves, thereby producing an electrical signal characteristic of the wavelength composition of the electromagnetic radiation; and
f. analyzing the electrical signal to produce the wavelength pattern of the electromagnetic spectral radiation.

34. The method as described in claim 33, wherein the first direction of linear polarization and the second direction of linear polarization are parallel.

35. A method for simultaneously measuring a plurality of spectral wavelengths present in fluorescence, comprising the steps of:
a. linearly polarizing the fluorescence having an electric field disposed in an arbitrary direction along a first direction;
b. resolving the electric field of the linearly polarized fluorescence along two orthogonal directions;
c. introducing a phase shift of greater than one wavelength of the longest wavelength component of the fluorescence between light waves associated with each of the resolved electric fields;
d. linearly polarizing the phase-shifted light waves along a second direction;
e. detecting the interference pattern generated from the interaction of the linearly polarized, phase shifted light waves, thereby producing an electrical signal characteristic of the wavelength composition of the fluorescence; and
f. analyzing the electrical signal to produce the wavelength pattern of the fluorescence.

36. The method as described in claim 35, wherein the first direction of linear polarization and the second direction of linear polarization are parallel.

* * * * *